(12) United States Patent
Hwang et al.

(10) Patent No.: US 6,625,480 B2
(45) Date of Patent: Sep. 23, 2003

(54) APPARATUS AND METHOD FOR MEASURING A CONCENTRATION OF A COMPONENT OF A TARGET MATERIAL

(75) Inventors: In-duk Hwang, Suwon (KR); Gil-won Yoon, Suwon (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/128,338

(22) Filed: Apr. 24, 2002

(65) Prior Publication Data
US 2002/0169368 A1 Nov. 14, 2002

(30) Foreign Application Priority Data
May 9, 2001 (KR) ........................................ 2001-25224

(51) Int. Cl.[7] ................ A61B 5/00; G01J 3/42
(52) U.S. Cl. ...................... 600/310; 356/320
(58) Field of Search ................ 600/310, 316, 600/322, 476; 356/300, 301, 319, 320, 326, 328; 422/82.05, 82.09

(56) References Cited
U.S. PATENT DOCUMENTS

| | | | |
|---|---|---|---|
| 5,037,200 A | * 8/1991 | Kodama | 356/301 |
| 5,086,229 A | 2/1992 | Rosenthal et al. | 250/341 |
| 5,222,495 A | 6/1993 | Clarke et al. | 128/633 |
| 5,553,616 A | * 9/1996 | Ham et al. | 600/316 |
| 5,828,452 A | * 10/1998 | Gillispie et al. | 256/318 |
| 6,061,582 A | 5/2000 | Small et al. | 600/316 |
| 6,152,876 A | 11/2000 | Robinson et al. | 600/322 |

* cited by examiner

Primary Examiner—Eric F. Winakur
(74) Attorney, Agent, or Firm—Lee & Sterba, P.C.

(57) ABSTRACT

Apparatus and method for measuring concentration of a component of target material including a pumping light source for emitting light; a first wavelength conversion unit for converting and outputting the light; a first beam splitting unit for splitting the converted light and directing a first light beam at the target material; a reference light generator for converting a second light beam to be parallel, dividing the parallel light beam by wavelengths, and outputting the result as reference light; a first collimating unit for converting light transmitted through the target material to be parallel and outputting the parallel light; a light intensity measuring unit for measuring the intensity of light from the first collimating unit and the reference light, by wavelengths, using the reference light; and a concentration measuring unit for measuring the concentration of the component based on the intensities measured by the light intensity measuring unit by wavelengths.

48 Claims, 9 Drawing Sheets

FIG. 10 under the US 6,625,480 B2

APPARATUS AND METHOD FOR MEASURING A CONCENTRATION OF A COMPONENT OF A TARGET MATERIAL

BACKGROUND OF THE INVENTION

1. Field of the Invention

The present invention relates to use of an optical fiber. More particularly, the present invention relates to an apparatus and method for measuring a concentration of each component of a target material using light having wavelengths discretely converted through an optical fiber.

2. Description of the Related Art

As a person's living environment and conditions continue to improve, one's interest in personal health increases. As a result, a variety of household medical devices, which allow the condition of a person's health to be easily checked at any time, have been developed.

In a human body, body fluids are circulated and adjusted so that the amount of each body fluid may be maintained within a particular normal range. Body fluids, for example, include blood, urine, interstitial fluid, sweat, and saliva. Particularly, the concentration of each component, such as sugar or protein, in body fluids such as blood or urine is very useful in determining a person's health condition. In addition, to determine a person's health condition, concentrations of glucose, hemoglobin, bilirubin, cholesterol, albumin, creatine, protein, and urea may be measured.

When a living body becomes sick, a change occurs in the composition and/or the amount of one or more components of body fluids. Accordingly, one's health condition may be checked by measuring a concentration of one or more components of a body fluid. For example, the concentration of blood glucose in a normal person is about 80 mg/dl before a meal and about 120 mg/dl after a meal. In order to maintain such a concentration of blood glucose in a living body, the pancreas secretes a proper amount of insulin before or after a meal so that the insulin may be absorbed into the liver and the cells of skeletal muscle. When the pancreas does not secrete enough insulin to maintain a normal blood glucose level due to illness or other reasons, however, a blood glucose level excessively increases. An excessive increase may cause a cardiac disorder, liver trouble, arteriosclerosis, hypertension, cataract, retinal hemorrhage, injury to nerves, hearing loss, amblyopia, or even death in a worst case. Accordingly, it is very important to be able to evaluate any change in a component of body fluids in an organism without being limited by time or location.

Two representative methods of measuring a concentration of a component of body fluids are an invasive method of directly taking a sample of a target material to measure the concentration of a component and a non-invasive method for measuring the concentration without taking a sample of a target material. According to a usual invasive method for measuring the concentration of a component of a body fluid, a blood sample is taken, a reaction between the blood sample and a diagnosis reagent is analyzed using clinical analysis apparatus, and the concentration of the component is measured based on the result of the analysis. In such an invasive method, however, the taking of blood samples may be painful and may expose a diabetic patient to a risk of infection. Moreover, it is difficult to monitor the patient continuously. Thus, in the case of an emergency, a patient may not be timely and properly treated. In addition, the invasive method requires the use of many expendable supplies, such as strips or reagents, which places a financial burden on a patient and causes environmental pollution. Accordingly, there is motivation to develop technology for measuring the concentration of blood glucose non-invasively for the purpose of controlling blood glucose in diabetics or checking a person's health condition.

In most spectroscopic methods used for measuring a concentration of a component of a body fluid in an organism, light having an optical wavelength of a visible ray or a near infrared ray (NIR) is radiated at a portion of tissue in the organism, and light reflected from or transmitted through the organism is detected to estimate the concentration of a component of the body fluid. Here, light having a wavelength most readily sensitive to a particular component to be measured and reference light having a wavelength within a band allowing influence by an interfering material to be effectively countervailed are necessary.

A conventional apparatus for measuring a concentration of a component measures a spectrum using a continuous wave (CW) light source and calculates the concentration from the measured spectrum or calculates the concentration using a plurality of light emitting diodes (LED) or laser diodes (LD) as a light source. However, since the concentration of a component to be measured is very low and the effect of scattering of light is greater than the influence of absorption of light in organic tissue and blood, a detected signal may be weak. Accordingly, a method for increasing the magnitude of a signal is required, but average energy applied to a body should be outside of a range in which the tissue of the body may be damaged. Particularly, in an NIR range of 700–2500 nm, a glucose absorption band is widely spread, and a glucose absorption peak is relatively small against a wide background spectrum with respect to water, so a signal to noise ratio is small. Accordingly, it is difficult to measure an accurate concentration.

SUMMARY OF THE INVENTION

It is a first feature of an embodiment of the present invention to provide an apparatus capable of easily generating light having a plurality of discrete wavelengths and radiating the generated light at a target material to measure a concentration of each component of the target material.

It is a second feature of an embodiment of the present invention to provide a method performed using the above apparatus to measure a concentration of each component of the target material.

To provide the first feature of an embodiment of the present invention, there is provided an apparatus for measuring a concentration of a component of a target material. The apparatus includes a pumping light source for emitting light having a single wavelength having peak power of at least a predetermined value; a first wavelength conversion unit for converting light incident from the pumping light source into light having at least one discrete wavelength and outputting the converted light; a first beam splitting unit for splitting the converted light incident from the first wavelength conversion unit into light beams and directing a first light beam at the target material; a reference light generator for converting a second light beam generated by the splitting performed in the first beam splitting unit to be parallel, dividing the parallel light beam by wavelengths, and outputting the result of the division as reference light; a first collimating unit for converting light transmitted through the target material to be parallel and outputting the parallel light; a light intensity measuring unit for measuring the intensity of light incident from the first collimating unit and the intensity of the reference light, by wavelengths, using the reference light; and a concentration measuring unit for measuring the concentration of the component based on the intensities measured by the light intensity measuring unit by wavelengths.

In another embodiment of the present invention, there is provided an apparatus for measuring a concentration of a component of a target material. The apparatus includes a pumping light source for emitting light having a single wavelength having peak power of at least a predetermined value; a second through 2V-th beam splitting units, wherein V is at least 2; a second through (V+1)-th wavelength conversion units; a total reflector; a reference light generator for converting a light beam generated by a splitting performed in each of the (V+1)-th through the 2V-th beam splitting units to be parallel, dividing the parallel light by wavelengths, and outputting the result of the division as reference light; a first collimating unit for converting light transmitted through the target material to be parallel and outputting the parallel light; a light intensity measuring unit for measuring the intensity of light incident from the first collimating unit and the intensity of the reference light, by wavelengths, using the reference light; and a concentration measuring unit for measuring the concentration of the component based on the intensities measured by the light intensity measuring unit by wavelengths, wherein the second beam splitting unit splits light incident from the pumping light source into light beams and outputs one of the light beams to the second wavelength conversion unit, the v-th ($3 \leq v \leq V$) beam splitting unit receives and splits one of light beams generated by the splitting performed in the (v−1)-th beam splitting unit into light beams and outputs one of the light beams to a v-th wavelength conversion unit, the total reflector totally reflects one of the light beams generated by the splitting performed in the V-th beam splitting unit to the (V+1)-th wavelength conversion unit, the w-th ($2 \leq w \leq V+1$) wavelength conversion unit converts incident light into light having at least one discrete wavelength and outputs the converted light, and the (V+w−1)-th beam splitting unit splits light incident from the w-th wavelength conversion unit into light beams and outputs one of the light beams at the target material.

To provide the second feature of an embodiment of the present invention, there is provided a method for measuring a concentration of a component of a target material. The method includes emitting light having a single wavelength having peak power of at least a predetermined value; converting the emitted light into light having at least one discrete wavelength; splitting the converted light into light beams, directing a first light beam at the target material, converting a second light beam to be parallel, and dividing the parallel converted second light beam by wavelengths to generate reference light; converting light transmitted through the target material to be parallel; measuring the intensity of the parallel converted light and the intensity of the reference light, by wavelengths; and measuring the concentration of the component based on the intensities measured by wavelengths.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

Korean Patent Application No. 2001-25224, filed May 9, 2001, and entitled: "Apparatus and Method for Measuring Concentration of Component in Target Material," is incorporated by reference herein in its entirety.

For the purpose of describing the preferred embodiments of the present invention in a clear manner and to differentiate the various elements of the embodiments as described in the following detailed description and appended claims, it is to be understood that as used herein "a first beam splitting unit" and "a second through (2V)-th beam splitting units" refer to a single beam splitting unit and "a first wavelength conversion unit" and "a second through (V+1)-th wavelength conversion units" refer to a single wavelength conversion unit in the description of the first embodiment and second embodiment, respectively. Accordingly, in the description of the second embodiment, although the term "a second beam splitting unit" is used, it is used only to differentiate the beam splitting units of the second embodiment from the "first beam splitting unit" of the first embodiment, i.e., in the second embodiment there is no "a first beam splitting unit." Similarly, in the description of the second embodiment, although the term "a second wavelength conversion unit" is used, it is used only to differentiate the wavelength conversion units of the second embodiment from the "first wavelength conversion unit" of the first embodiment, i.e., in the second embodiment there is no "a first wavelength conversion unit."

Hereinafter, the configurations and operations of embodiments of an apparatus for measuring a concentration of a component of a target material according to the present invention, and a method performed using the apparatus according to the present invention will now be described in detail with reference to the attached drawings.

Figure 1:
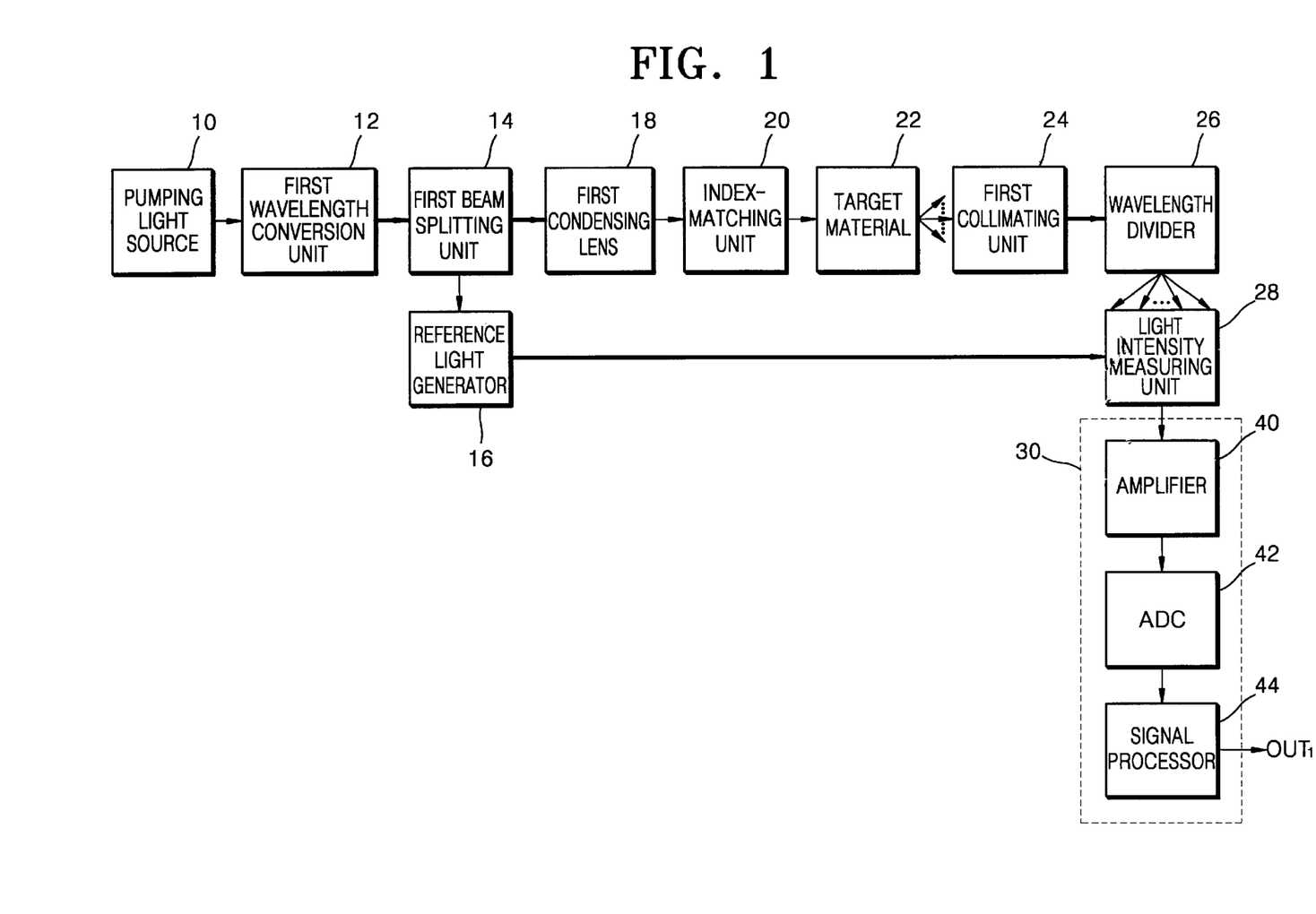
FIG. 1 is a block diagram of a first embodiment of an apparatus for measuring a concentration of a component of a target material according to an embodiment of the present invention.

FIG. 1 is a block diagram of a first embodiment of an apparatus for measuring a concentration of a component of a target material according to an embodiment of the present invention. The apparatus includes a pumping light source 10, a first wavelength conversion unit 12, a first beam splitting unit 14, a reference light generator 16, a target material 22, a first collimating unit 24, a light intensity measuring unit 28, and a concentration measuring unit 30. The apparatus may further include a first condensing lens 18, an index-matching unit 20, and a wavelength divider 26. The concentration measuring unit 30 may include an amplifier 40, an analog-to-digital converter (ADC) 42, and a signal processor 44.

Figure 2:
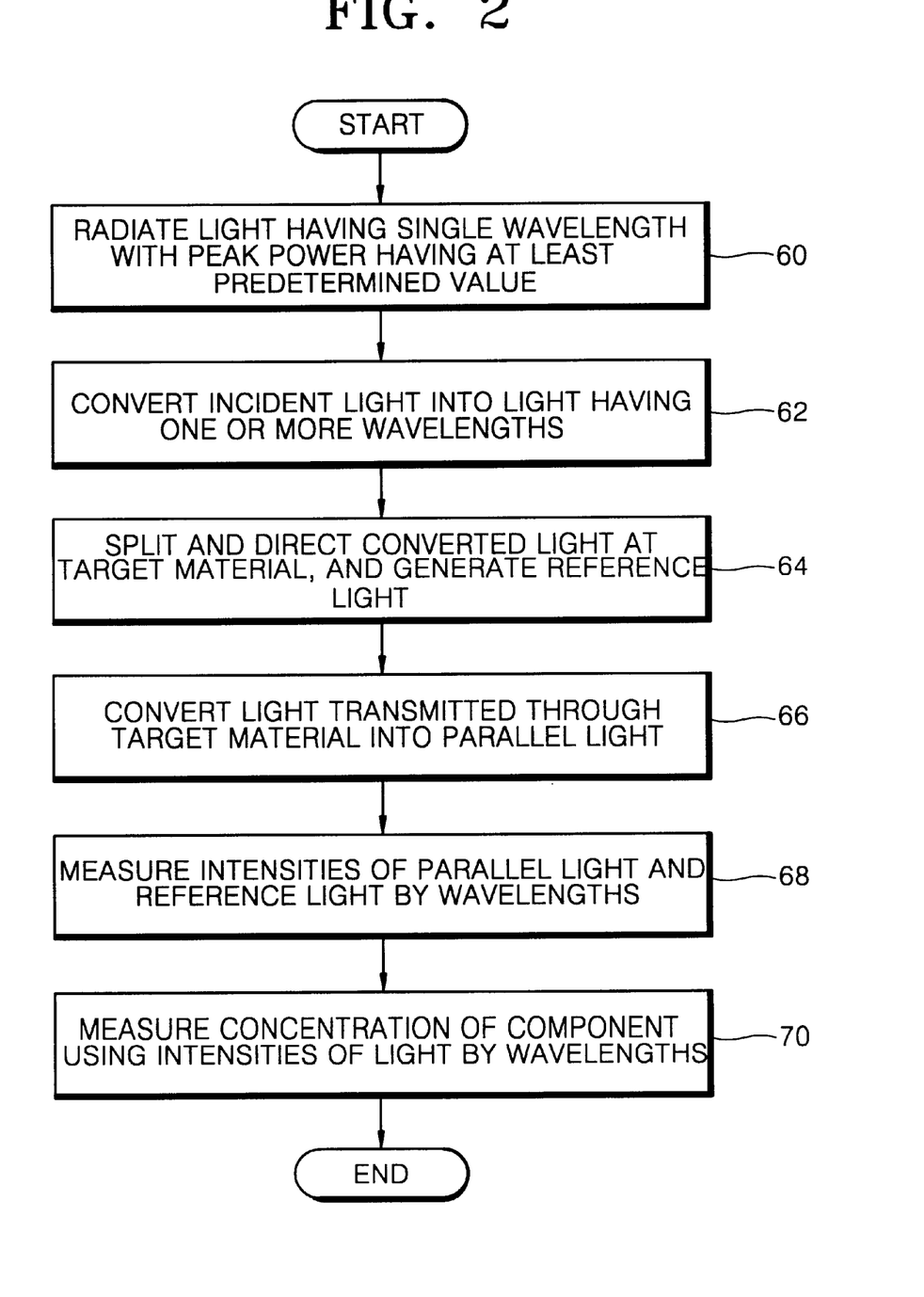
FIG. 2 is a flowchart of a method for measuring a concentration of a component of a target material according to an embodiment of the present invention, which is performed using the apparatus of FIG. 1.

FIG. 2 is a flowchart of a method for measuring a concentration of a component of a target material according to an embodiment of the present invention, which is performed using the apparatus of FIG. 1. In steps 60 and 62, light having one or more discrete wavelengths is generated from incident light having a single wavelength. In steps 64 through 68, the generated light is radiated at the target material 22, and the intensity of light which is transmitted through the target material 22 is measured by the wavelengths together with the intensity of reference light. In step 70, the concentration of a component of the target material 22 is measured using the measured intensity.

Referring to FIGS. 1 and 2, according to a first embodiment of the present invention, in step 60, the pumping light source 10 of the apparatus for measuring a concentration of a component of a target material radiates light having a single wavelength with a peak power having at least a predetermined value at the first wavelength conversion unit 12. For this, the pumping light source 10 may be realized as a pulse laser or a continuous wave (CW) laser. Here, the pulse laser may be an Nd:YAG laser, an Ho:YAG laser, a Tm:YAG laser, an optical parametric oscillation (OPO) laser, a solid-state laser, or an optical fiber laser. The pulse laser may be realized as a 1064 nm pulse laser, a 1300 nm pulse laser, an Ho:YAG laser emitting a beam with a wavelength of 2 μm, or a Tm:YAG laser emitting a beam with a wavelength of about 2 μm. The CW laser may be realized as a laser diode generating light having a wavelength of 1480 nm.

After step 60, in step 62, the first wavelength conversion unit 12 receives the light radiated by the pumping light source 10, converts the incident light into light having one or more discrete wavelengths, and outputs the converted light to the first beam splitting unit 14.

After step 62, in step 64, the first beam splitting unit 14 splits the light having one or more wavelengths output from the first wavelength conversion unit 12 into two light beams. The first beam splitting unit 14 directs one of the light beams at the target material 22, and outputs another one of the light beams to the reference light generator 16. Then, the reference light generator 16 converts the light beam received from the first beam splitting unit 14 to be parallel, divides the parallel light beam into wavelengths, and outputs the result of the division as reference light to the light intensity measuring unit 28. The reference light generator 16 may include a collimator (not shown) for converting the light beam received from the first beam splitting unit 14 to be parallel and a diffraction grating (not shown) for dividing the parallel light beam converted by the collimator into wavelengths and outputting the result of the division as reference light to the light intensity measuring unit 28.

According to an embodiment of the present invention, the apparatus for measuring a concentration of a component of a target material, shown in FIG. 1, may further include the first condensing lens 18 and/or the index-matching unit 20. When both the first condensing lens 18 and the index-matching unit 20 are provided together, the index-matching unit 20 is disposed between the first condensing lens 18 and the target material 22.

In order to radiate light of high intensity at the target material, the first condensing lens 18 condenses the light beam from the first beam splitting unit 14 and transmits the result of the condensing to the index-matching unit 20 or the target material 22. The index-matching unit 20 receives the light beam from the first light beam splitting unit 14 or the result of the condensing performed by the first condensing lens 18 and transmits it to the target material 22. In other words, the index-matching unit 20 matches the refractive index of the outside of the target material 22 with the refractive index of the inside of the target material 22 to improve an overall signal to noise ratio (SNR).

According to an embodiment of the present invention, the target material 22 may be a living body, an organism or a sample cuvette. When the target material 22 is a living body, a light beam output from the first beam splitting unit 14 is radiated through the first condensing lens 18 and/or the index-matching unit 20 onto an organic tissue such as a skin surface. When the target material 22 is an organism, an apparatus and method according to an embodiment of the present invention measure the concentration of a component non-invasively. When the target material 22 is a sample cuvette, an apparatus and method according to an embodiment of the present invention measure the concentration of a component invasively.

After step 64, in step 66, the first collimating unit 24 converts dispersed light transmitted through the target material 22 into parallel light and outputs the parallel light. The first collimating unit 24 may be realized by connecting a plurality of lenses (not shown) in series.

After step 66, in step 68, the light intensity measuring unit 28 measures the intensity of the parallel light received from the first collimating unit 24 and the intensity of the reference light received from the reference light generator 16 by wavelengths and outputs the result of the measurement to the concentration measuring unit 30. In order to allow the light intensity measuring unit 28 to measure the intensity of parallel light received from the first collimating unit 24 by wavelengths, the apparatus shown in FIG. 1 may further include the wavelength divider 26 which divides the light received from the first collimating unit 24 by wavelengths and outputs the light of different wavelengths to the light intensity measuring unit 28. The wavelength divider 26 may be included in the light intensity measuring unit 28. Then, the light intensity measuring unit 28 measures the intensity of the light output from the wavelength divider 26 and the intensity of the reference light received from the reference light generator 16, by wavelengths.

According to an embodiment of the present invention, the light intensity measuring unit 28 may be realized as a near infrared light intensity measuring unit (not shown) or an array light intensity measuring unit (not shown) that measures the intensity of light output from the first collimating unit 24 or the wavelength divider 26 and the intensity of reference light, by wavelengths. Here, the near infrared light intensity measuring unit or the array light intensity measuring unit may be manufactured using Si, Ge, InGaAs, InAs, InSb, InS, or PbS.

After step 68, in step 70, the concentration measuring unit 30 measures the concentration of a certain component of the target material 22 using the intensity of light of different wavelengths measured by the light intensity measuring unit 28 and outputs the measured concentration through an output terminal $OUT_1$.

Figure 3:
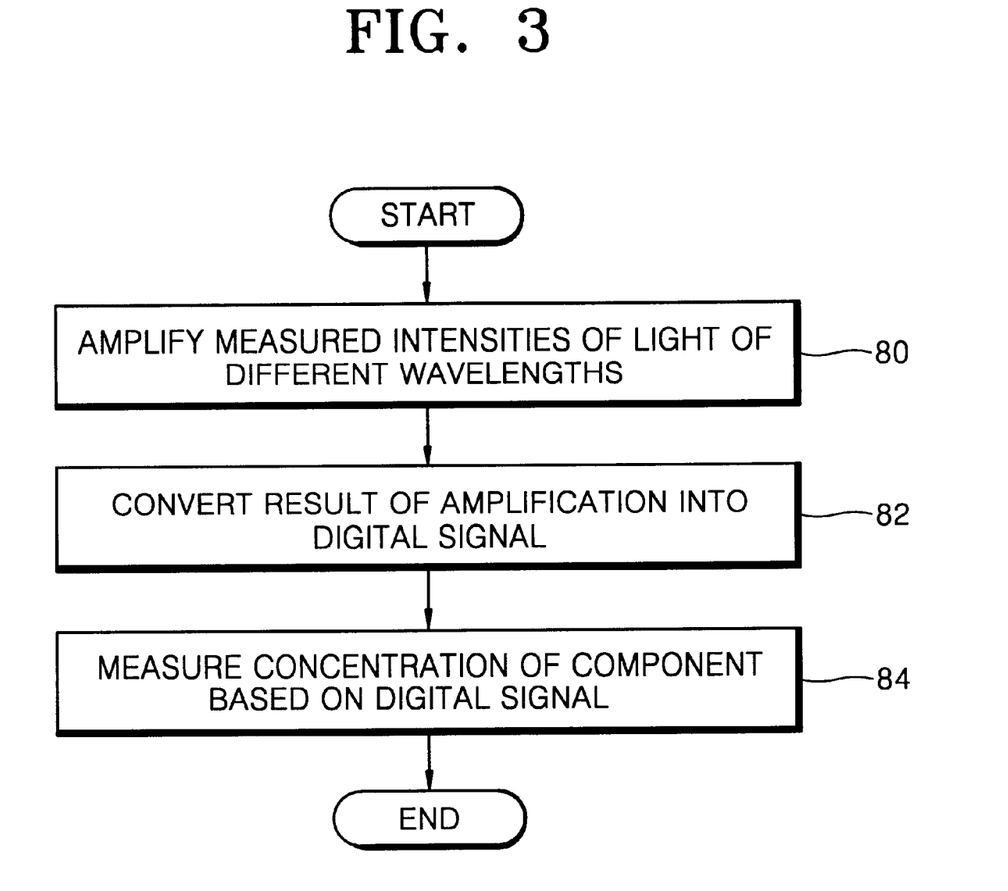
FIG. 3 is a flowchart of an embodiment of step 70 shown in FIG. 2 according to an embodiment of the present invention.

FIG. 3 is a flowchart of an embodiment of step 70 shown in FIG. 2 according to an embodiment of the present invention. Step 70 may include, as a step 80, amplifying the measured intensity, as a step 82, converting the result of the amplification into a digital signal, and, as a step 84, measuring the concentration of a component based on the digital signal.

In step 80, the amplifier 40 shown in FIG. 1 amplifies the intensity of light of different wavelengths measured by the light intensity measuring unit 28 and outputs the result of amplification to the ADC 42. After step 80, in step 82, the ADC 42 converts the result of the amplification received from the amplifier 40 into a digital form and outputs the result of the conversion to the signal processor 44 in the form of a digital signal. After step 82, in step 84, the signal processor 44 performs signal processing on the digital signal received from the ADC 42 to analyze the digital signal, compares and analyzes differences in the intensity of light transmitted through or reflected from the target material 22 between the wavelengths or differences between spectra to estimate the concentration of a certain component of the target material 22, and outputs as a measured concentration the result of the estimation to the output terminal $OUT_1$. The signal processor 44 has previously made and stored a prediction model formula defining the relation between the absorbency of light radiated at the target material 22 at different wavelengths and the concentrations of a component of the target material 22. Here, the signal processor 44 calculates the absorbency of light at the different wavelengths from the digital signal received from the ADC 42 and substitutes the calculated absorbency into the prediction model formula to estimate the concentration of the component.

Unlike the apparatus of FIG. 1, an apparatus for measuring a concentration of a component of a target material according to another embodiment of the present invention may convert the wavelength(s) of light generated from the pumping light source 10 as follows.

Figure 4:
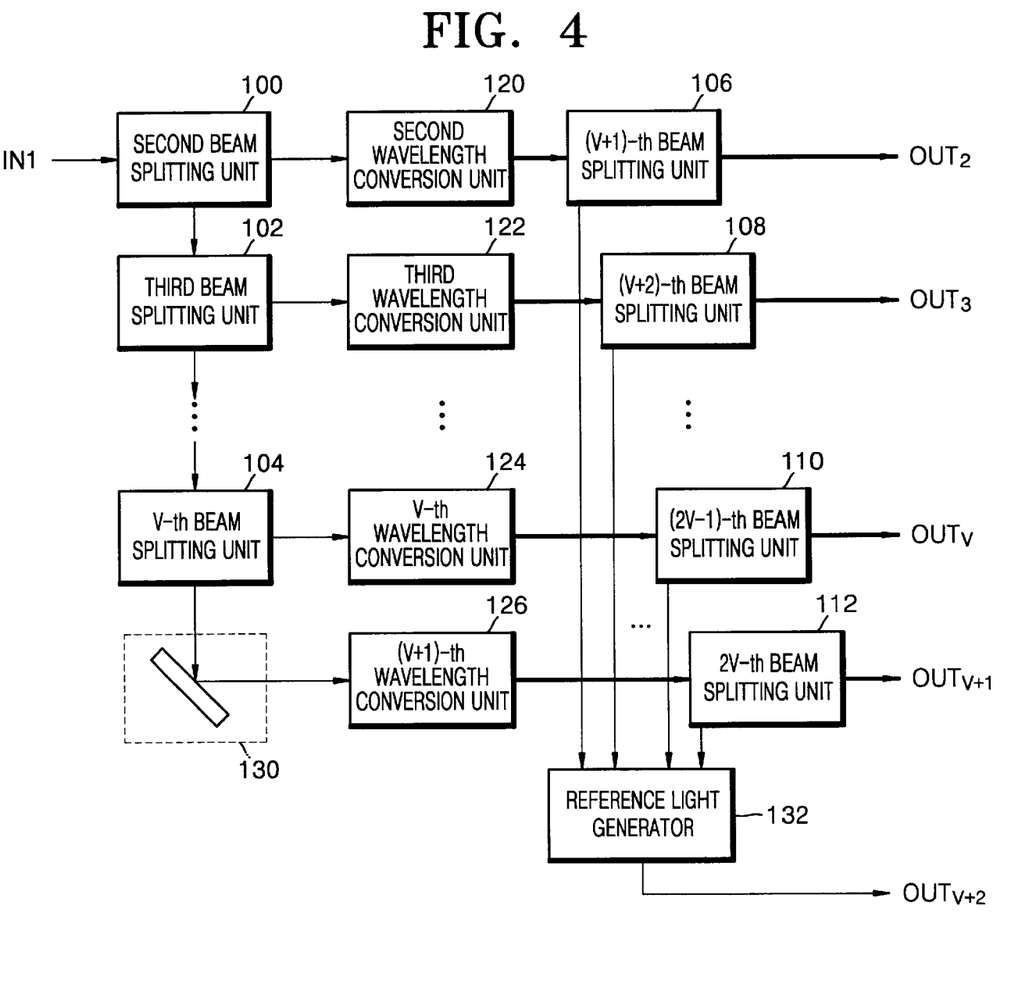
FIG. 4 is a block diagram of a second embodiment of an apparatus for measuring a concentration of a component of a target material according to an embodiment of the present invention.

FIG. 4 is a block diagram of a second embodiment of an apparatus for measuring a concentration of a component of a target material according to an embodiment of the present invention. The second embodiment includes second through 2V-th (V is at least 2) beam splitting units 100, 102, ..., 104, 106, 108, ..., 110, and 112, second through (V+1)-th wavelength conversion units 120, 122, ..., 124, and 126, a total reflector 130, and a reference light generator 132.

Figure 5:
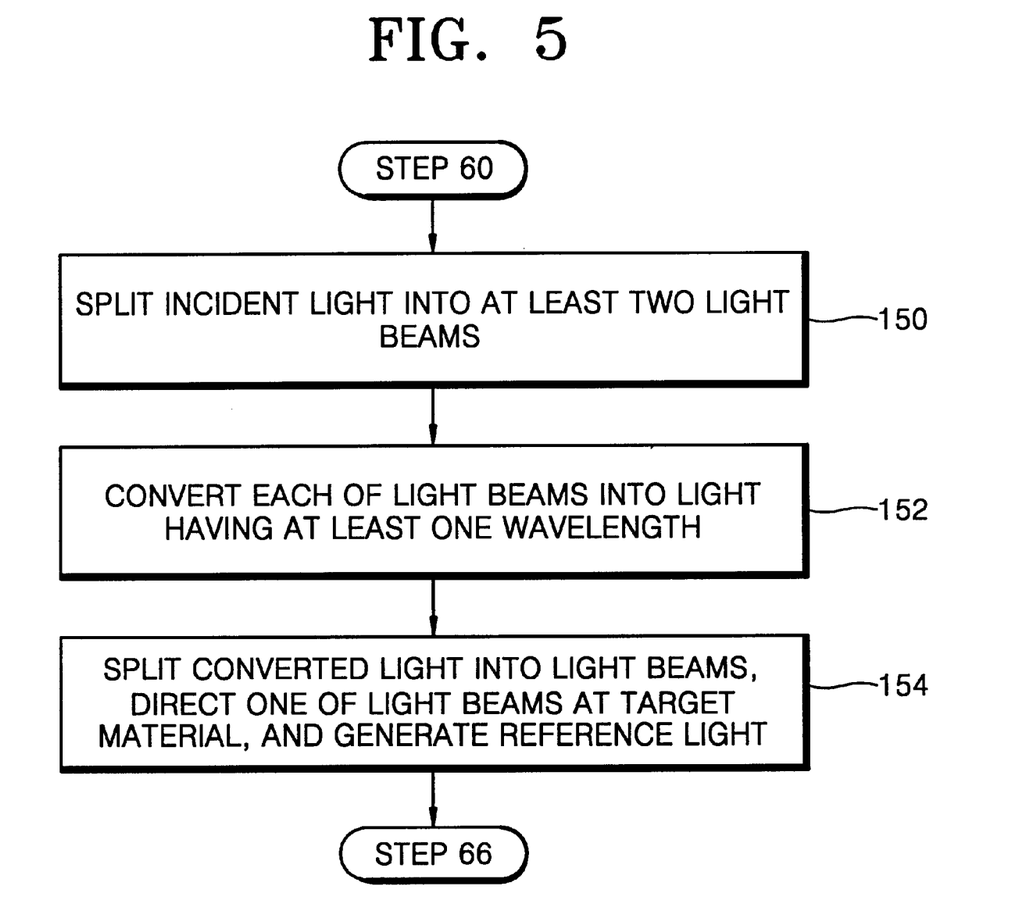
FIG. 5 is a flowchart of a method for measuring a concentration of a component of a target material according to an embodiment of the present invention, which is performed using the apparatus of FIG. 4.

FIG. 5 is a flowchart of a method for measuring a concentration of a component of a target material according to an embodiment of the present invention, which is performed using the apparatus of FIG. 4. The method includes splitting incident light into at least two light beams in step 150, after step 60 of FIG. 2, converting the wavelength of each of the light beams in step 152, and radiating light having the converted wavelengths at a target material while generating reference light in step 154, and proceeds to step 66.

According to the second embodiment of the present invention, the first wavelength conversion unit 12, the first beam splitting unit 14, and the reference light generator 16 shown in FIG. 1 may be replaced by the second through 2V-th beam splitting units 100, 102, ..., 104, 106, 108, ..., 110, and 112, the second through (V+1)-th wavelength conversion units 120, 122, ..., 124, and 126, the total reflector 130, and the reference light generator 132, shown in FIG. 4.

After step 60, in step 150, the second through V-th beam splitting units 100, 102, ..., and 104 split incident light, which is emitted from the pumping light source 10 of FIG. 1 and received through an input terminal IN1, into at least two light beams. Here, the second beam splitting unit 100 splits the incident light received from the pumping light source 10 through the input terminal IN1 into light beams. The second beam splitting unit 100 outputs one of the light beams to the second wavelength conversion unit 120 and outputs another one of the light beams to the third beam splitting unit 102. A v-th ($3 \leq v \leq V$), one of the third through V-th beam splitting units 102, ..., 104, receives one of light beams generated by the (v−1)-th beam splitting unit, splits the received light beam into light beams, and outputs one of the light beams to a v-th wavelength conversion unit 122, ..., or 124. Here, when v≠V, the v-th beam splitting unit outputs another one of the light beams to a (v+1)-th beam splitting unit.

After step 150, in step 152, each of the second through (V+1)-th wavelength conversion units 120, 122, ..., 124, and 126 converts a light beam received from a corresponding beam splitting unit 100, 102, ..., or 104 into light having at least one discrete wavelength and outputs the converted light to a corresponding beam splitting units 106, 108, ..., 110 and 112. For example, a w-th ($2 \leq w \leq V+1$) wavelength conversion unit, one of the second through (V+1)-th wavelength conversion units 120, 122, ..., 124 and 126, converts incident light into light having at least one discrete wavelength and outputs the converted light to a (V+w−1)-th beam splitting unit 106, 108, ..., 110 or 112. Here, the total reflector 130 receives another one of light beams generated by the V-th beam splitting unit 104 and totally reflects the light beam to the (V+1)-th wavelength conversion unit 126.

After step 152, in step 154, each of the (V+1)-th through 2V-th beam splitting units 106, 108, ..., 110, and 112 splits the converted light received from the corresponding one of the second through (V+1)-th wavelength conversion units 120, 122, ..., 124, and 126 into light beams. Each of the (V+1)-th through 2V-th beam splitting units 106, 108, ..., 110, and 112 directs one of the light beams at the target material 22 through a corresponding one of output terminals $OUT_2$ through $OUT_{V+1}$ and outputs another one of the light beams to the reference light generator 132. For example, a (V+w−1)-th beam splitting unit, one of the (V+1)-th through 2V-th beam splitting units 106, 108, ..., 110 and 112, splits light received from a w-th wavelength conversion unit 120, 122, ..., 124 or 126 into light beams, directs one of the light beams at the target material 22 through an output terminal $OUT_w$, and outputs another one of the light beams to the reference light generator 132.

Here, the first condensing lens 18 and/or the index-matching unit 20, shown in FIG. 1, may be provided between the (V+w−1)-th beam splitting unit and the target material 22. When the first condensing lens 18 and/or the index-matching unit 20 is provided between the (V+w−1)-th beam splitting unit and the target material 22, the first condensing lens 18 condenses a light beam received from the (V+w−1)-th beam splitting unit and transmits the result of the condensing at the index-matching unit 20. The index-matching unit 20 transmits light condensed by the first condensing lens 18 at the target material 22.

In addition, in step 154, the reference light generator 132 converts the light beams received from the (V+1)-th through 2V-th beam splitting units 106, 108, ..., 110 and 112 into parallel light, divides the parallel light by wavelengths, and outputs as reference light the results of the division to the light intensity measuring unit 28 of FIG. 1 through the output terminal $OUT_{V+2}$. The reference light generator 132 may include a collimator (not shown) and a diffraction grating (not shown) similar to the reference light generator (16 of FIG. 1).

Each of the first through (V+1)-th wavelength conversion units 12, 120, 122, ..., 124 and 126 shown in FIGS. 1 and 4 is capable of converting incident light into light having any discrete wavelengths within the ranges of ultraviolet, visible and near infrared wavelengths. For example, each of the first through (V+1)-th wavelength conversion units 12, 120, 122, ..., 124 and 126 is capable of converting the wavelength of incident light into a wavelength having an absorption in blood glucose.

Hereinafter, the configuration and operation of an embodiment of each of the first through (V+1)-th wavelength conversion units 12, 120, 122, ..., 124 and 126 according to an embodiment of the present invention will be described with reference to the attached drawings.

Figure 6:
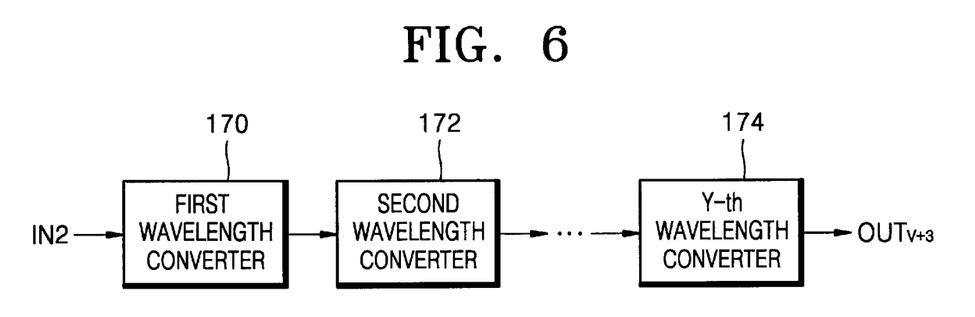
FIG. 6 is a block diagram of an embodiment of each of the first through (V+1)-th wavelength conversion units shown in FIGS. 1 and 4 according to an embodiment of the present invention.

FIG. 6 is a block diagram of an embodiment of each of the first through (V+1)-th wavelength conversion units 12, 120, 122, ..., 124, and 126 shown in FIGS. 1 and 4 according to an embodiment of the present invention. Each wavelength conversion unit includes first through Y-th (Y is at least 1) wavelength converters 170, 172, ..., 174 connected in series.

A y-th ($1 \leq y \leq Y$) wavelength converter, one of the first through Y-th wavelength converters 170, 172, ..., and 174, condenses incident light and converts it into light having one or more wavelengths and outputs the converted light in parallel. For example, the first wavelength converter 170 condenses light received through an input terminal IN2, converts it into light having at least one discrete wavelength, and outputs the converted light to the second wavelength converter 172 in parallel. The Y-th wavelength converter 174 condenses light received from a (Y-1)-th wavelength converter, converts it into light having at least one discrete wavelength, and outputs the converted light in parallel through an output terminal $OUT_{V+3}$.

Figure 7:
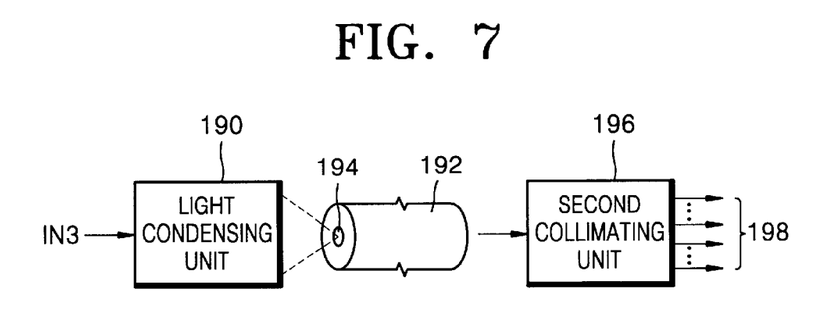
FIG. 7 is a block diagram of an embodiment of the Y-th wavelength converter of FIG. 6 according to an embodiment of the present invention.

FIG. 7 is a block diagram of an embodiment of a y-th wavelength converter of FIG. 6 according to an embodiment of the present invention. The y-th wavelength converter includes a light condensing unit 190, an optical fiber 192 having a core 194, and a second collimating unit 196.

Referring to FIG. 7, the light condensing unit 190 focuses light incident through an input terminal IN3 on an incident surface of the core 194 of the optical fiber 192. The light condensing unit 190 may be realized as a second condensing lens (not shown) or a tapered fiber that condenses light incident through the input terminal IN3 and efficiently emits the condensed light to the light incident surface of the core 194 of the optical fiber 192. When the light condensing unit 190 is realized as a tapered fiber, optical coupling efficiency may be increased by fusion splicing the tapered fiber and the optical fiber 192 together.

The optical fiber 192 receives the condensed light from the light condensing unit 190 and emits light having at least one discrete wavelength, which is frequency-shifted from an original wavelength due to a non-linear Raman effect, to the second collimating unit 196. Here, in order to generate the non-linear Raman effect in the optical fiber 192, the peak power value of light incident through the input terminal IN3 should be at least a predetermined value. The predetermined value is determined in accordance with the length and core diameter of the optical fiber 192. Hereinafter, the non-linear Raman effect generated by the optical fiber 192 of FIG. 7 will be described.

The spectra of a plurality of discrete wavelengths may be effectively obtained from the optical fiber 192 of a non-linear medium using the Raman effect. When light with a peak power having at least a predetermined value is incident onto the core 194 of the optical fiber 192, the incident light interacts with the optical phonons of the optical fiber 192 so as to scatter, so the incident light may be converted to Stokes light. Here, the Stokes light has a longer wavelength than the incident light. The frequency shift of the Stokes light is determined by a phonon frequency. Spontaneous Raman emission spectra for silicate, germanite, and phosphate glasses show a broad band of frequencies associated with the amorphous nature of oxide glasses. In addition, different kinds of glasses have different spectral features and different Raman scattering cross sections.

Since stimulated Raman scattering is coherent, unlike spontaneous Raman scattering, scattering light progresses only in a direction satisfying the law of conservation of momentum.

Figure 8:
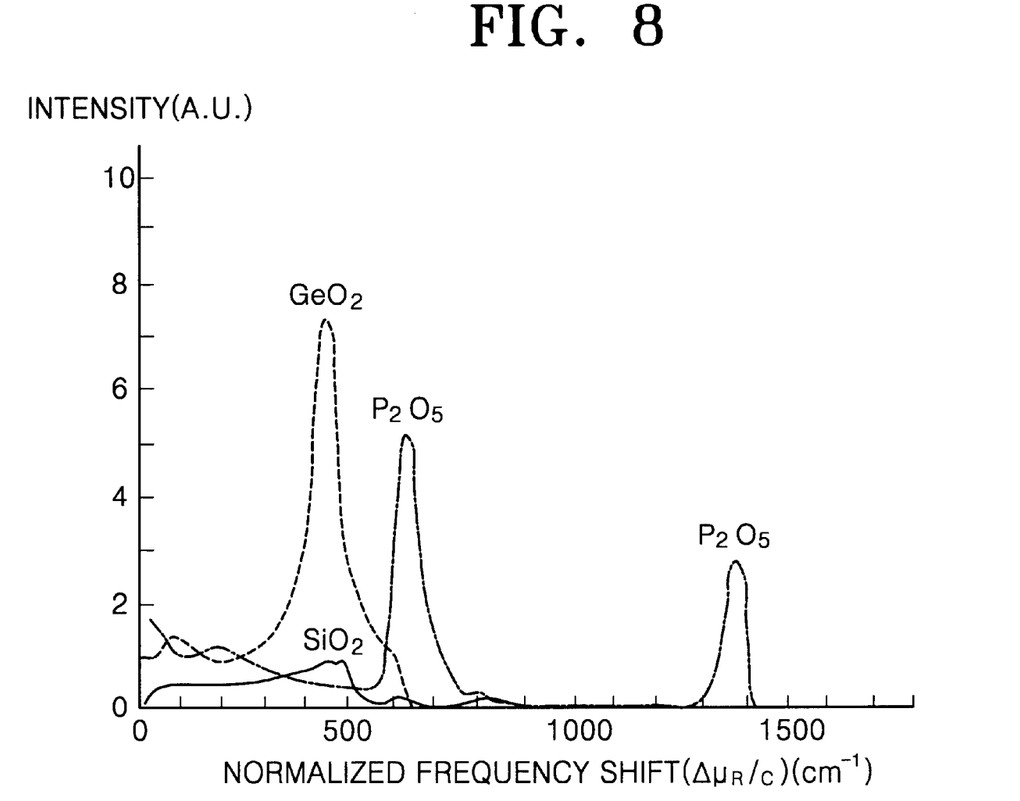
FIG. 8 is a graph of a Raman frequency shift versus a Raman gain coefficient when the core of an optical fiber is doped with various materials.

FIG. 8 is a graph of a Raman frequency shift $\Delta u_R$ versus a Raman gain coefficient when the core 194 of the optical fiber 192 is doped with various materials, i.e., $SiO_2$, $GeO_2$, and $P_2O_5$. The horizontal axis denotes the frequency shift which is normalized by the speed of light "c." The vertical axis denotes intensity. In the graph, A.U. denotes arbitrary units.

Referring to FIG. 8, since the peak Raman scattering cross-section of pure $GeO_2$ is roughly 10 times larger than that of pure silica, it is easy to obtain a high Raman gain with incident light having low intensity. An optical fiber doped with silica has a peak Raman gain at a normalized frequency shift of 440 $cm^{-1}$, and an optical fiber doped with Ge has a peak Raman gain at a normalized frequency shift of 490 $cm^{-1}$. The additional peak Raman gain of glass of $P_2O_5$ at a normalized frequency shift of 1330 $cm^{-1}$, may be very useful for achieving a large degree of frequency conversion into a Stokes component at one time. Generally, a Raman spectrum with respect to a high-silica optical fiber in which dopant glass has a relatively lower molecular percentage than silica glass is mainly influenced by a spectrum with respect to $SiO_2$.

A wavelength of Stokes light newly generated by stimulated Raman scattering within an optical fiber is calculated according to Equation (1).

$$w_s = w_p - nw_v \quad (1)$$

Here, $w_p$ denotes the pump frequency of incident light, $w_s$ denotes the frequency of Stokes light, $w_v$ denotes an internal vibration frequency of glass fiber, and n=1, 2, 3, ....

A Stokes component generated when a silica optical fiber is used as a Raman medium is amplified throughout the line width of Raman gain and particularly amplified fastest at a maximum of the gain. Accordingly, cascade Stokes waves of high order having a normalized frequency shift of 440 $cm^{-1}$ corresponding to the maximum gain in the stimulated Raman scattering may be generated. For example, when the wavelength of light incident on the core 194 of the optical fiber 192 is 1.064 μm, light emitted from the optical fiber 192 may have wavelengths of 1.12 μm, 1.18 μm, 1.23 μm, 1.31 μm, 1.39 μm, 1.48 μm, 1.58 μm, and 1.70 μm.

The second collimating unit 196 converts the light emitted from the optical fiber 192 to be parallel and emits parallel light 198.

According to an embodiment of the present invention, the wavelength of light incident on the second collimating unit 196 changes depending on a component with which the core 194 of the optical fiber 192 of FIG. 7 is doped, that is, depending on whether the core 194 is made of pure silica or doped with $GeO_2$ or $P_2O_5$. In other words, referring to FIG. 8, when a component with which the core 194 is doped is changed, light emitted from the optical fiber 192 has different discrete wavelengths even if light having the same wavelength is incident on the optical fiber 192. Accordingly, when the cores 194 of the optical fibers 192 included in the first through Y-th wavelength converters 170, 172, . . . , and 174, in the first wavelength conversion unit (12 of FIG. 1) or each of the second through (V+1)-th wavelength conversion units 120, 122, . . . , 124, and 126 of FIG. 4, are doped with different components, light having a variety of discrete wavelengths may be radiated at the target material 22.

The optical fiber 192 shown in FIG. 7 may be a single-mode or multi-mode step-index optical fiber or it may be a single-mode or multi-mode graded-index optical fiber.

When the target material 22 is a body fluid, an apparatus and method for measuring a concentration of a component according to an embodiment of the present invention easily generate discrete wavelengths corresponding to the absorption spectrum of a component of the body fluid and radiate the discrete wavelengths at the target material 22, thereby invasively or non-invasively measuring the concentration of the component. Hereinafter, to more clearly illustrate the present invention, it will be assumed that the target material 22 is an organism, that a body fluid component whose concentration is to be measured is glucose, that wavelengths of 1200 nm and 1300 nm, whose absorption spectra scarcely change in response to a change in the concentration of glucose in a target material, are selected as reference wavelengths used for measuring the concentration of glucose, and that V=2. The following description concerns the configuration and operation of an apparatus for measuring the concentration of a component of a target material according to an embodiment of the present invention.

Figure 9:
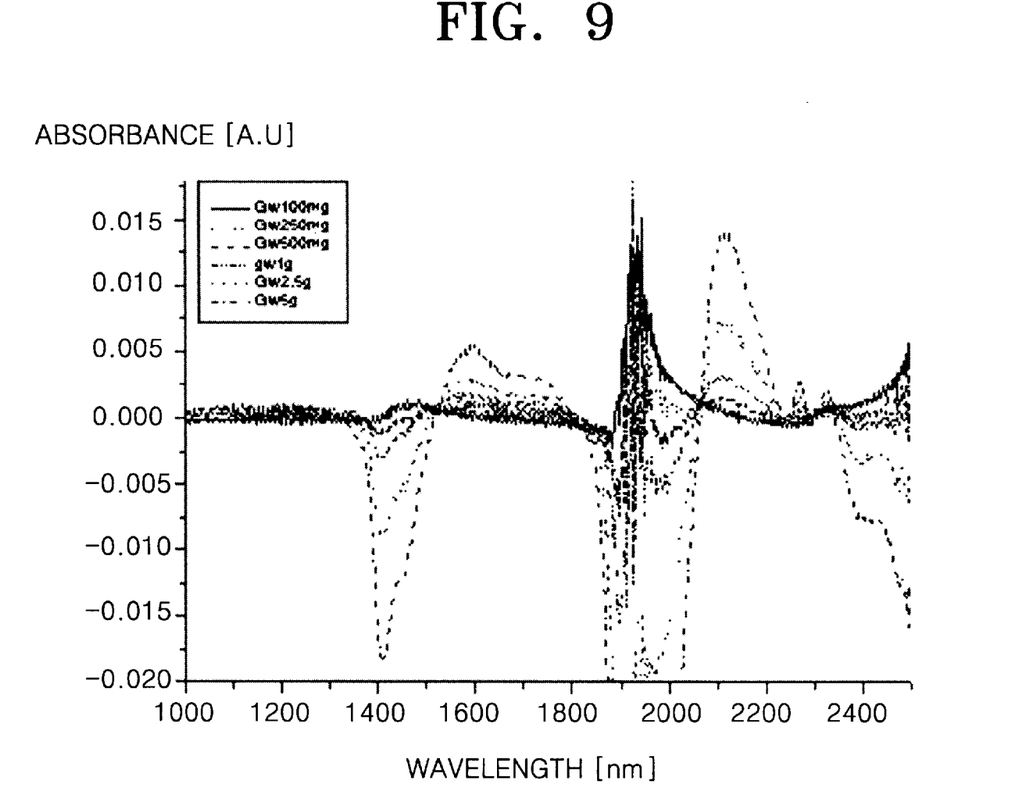
FIG. 9 is a graph of absorption spectrums of an aqueous glucose solution, from which water spectrum is subtracted, by wavelengths.

FIG. 9 is a graph of absorption spectrums of an aqueous glucose (Gw) solution, from which water spectrum is subtracted, by wavelengths. The horizontal axis denotes a wavelength. The vertical axis denotes absorbance.

As shown in FIG. 9, wavelengths exhibiting large absorption in glucose are in the ranges of 1500–1700 nm and 2050–2200 nm. In order to radiate light having wavelengths within these ranges at the target material 22, i.e., an organism, the apparatus for measuring the concentration of a component according to an embodiment of the present invention shown in FIG. 4 converts the wavelength of incident light as follows.

Figure 10:
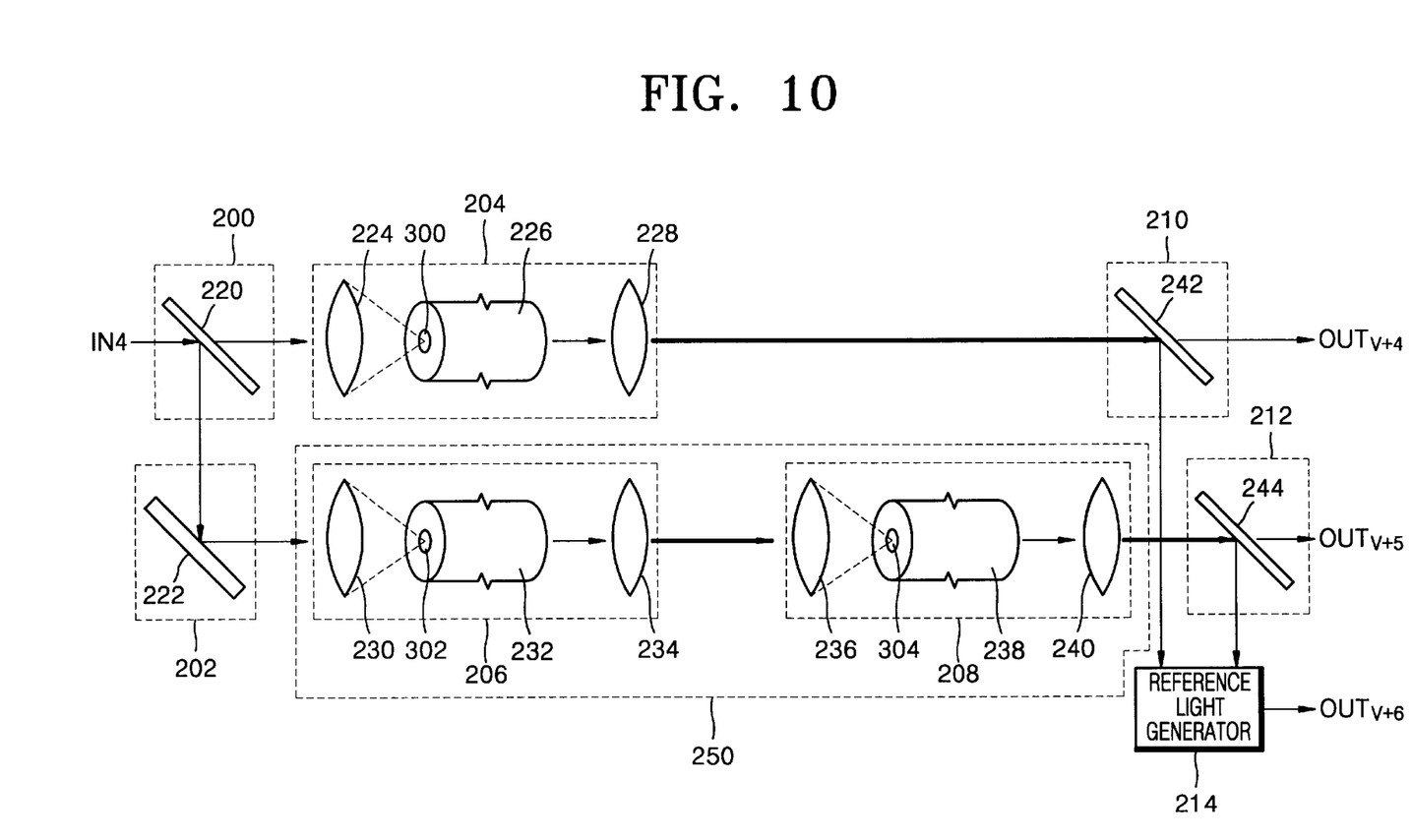
FIG. 10 is a block diagram of an apparatus, which generates light having wavelengths of 1200 nm, 1300 nm, and 1600 nm, for measuring a concentration of a component according to an embodiment of the present invention.

FIG. 10 is a block diagram of an apparatus, which generates light having wavelengths of 1200 nm, 1300 nm, and 1600 nm, for measuring a concentration of a component according to an embodiment of the present invention. The apparatus includes beam splitting units 200, 210, and 212, a total reflector 202, wavelength conversion units 204 and 250, and a reference light generator 214.

The beam splitting units 200, 210, and 212, wavelength conversion units 204 and 250, and reference light generator 214 correspond to and perform the same functions as the second through fourth beam splitting units 100, 106, and 112, the second and third wavelength conversion units 120 and 126, and the reference light generator 132, respectively, as shown in FIG. 4. In addition, each of condensing lenses 224, 230, and 236 provided in the wavelength converters 204, 206 and 208, respectively, corresponds to the light condensing unit (190 of FIG. 7). Each of collimators 228, 234, and 240 corresponds to the second collimating unit (196 of FIG. 7). The beam splitting units 200, 210, and 212 are realized as beam splitters 220, 242, and 244, respectively.

The beam splitting unit 200 of FIG. 10 splits light having a wavelength of 1064 nm incident from the pumping light source (10 of FIG. 1) through an input terminal IN4 into light beams, that is, the beam splitting unit 200 splits the energy of incident light and outputs one of the resulting light beams, which has a wavelength of 1064 nm, to the wavelength conversion unit 204 and outputs another resulting light beam, which has a wavelength of 1064 nm, to the total reflector 202. The total reflector 202 totally reflects the light beam received from the beam splitting unit 200 to the wavelength conversion unit 206. The total reflector 202 may be realized as a total reflecting mirror 222. Here, when a core 300 of an optical fiber 226 in the wavelength converter 204 is made of silica or doped with germanium (Ge), when a core 302 of an optical fiber 232 of the wavelength converter 206 in the wavelength conversion unit 250 is doped with phosphorous (P), and when a core 304 of an optical fiber 238 of the wavelength converter 208 in the wavelength conversion unit 250 is doped with germanium (Ge), the wavelength converters 204, 206 and 208 operate as follows.

The condensing lens 230 of the wavelength converter 206 condenses and transmits the light having a wavelength of 1064 nm, which is then totally reflected, from the total reflector 202 to the core 302 of the optical fiber 232. The optical fiber 232 converts the light having a wavelength of 1064 nm condensed by the condensing lens 230 into light having a wavelength of 1480 nm due to the Raman effect and emits the light having a wavelength of 1480 nm to the collimator 234. The collimator 234 converts the light emitted from the optical fiber 232 into parallel light and transmits the parallel light to the wavelength converter 208. Similarly, the wavelength converter 208 receives the light having a wavelength of 1480 nm from the wavelength converter 206, converts the received light into light having a wavelength of 1600 nm, and emits the converted light to the beam splitting unit 212. Accordingly, the beam splitter 244, by which the beam splitting unit 212 is implemented, splits the light having a wavelength of 1600 nm and directs one beam at the target material 22 through an output terminal $OUT_{V+5}$ and the other beam at the reference light generator 214.

Here, the condensing lens 224 of the wavelength converter 204 condenses and transmits one of the light beams output from the beam splitting unit 200 having a wavelength of 1064 nm to the core 300 of the optical fiber 226. The optical fiber 226 converts the light having a wavelength of 1064 nm condensed by the condensing lens 224 into light having wavelengths of 1200 nm and 1300 nm due to a Raman effect and emits the light having wavelengths of 1200 nm and 1300 nm to the collimator 228. The collimator 228 converts the light emitted from the optical fiber 226 into parallel light and transmits the parallel light to the beam splitting unit 210. Accordingly, the beam splitter 242 by which the beam splitting unit 210 is implemented directs the light having wavelengths of 1200 nm and 1300 nm at the target material 22 through an output terminal $OUT_{V+4}$ and at the reference light generator 214.

The reference light generator 214 receives light having wavelengths of 1200 nm, 1300 nm, and 1600 nm from the beam splitting units 210 and 212, converts the light to be parallel, divides the converted light by wavelengths, and outputs as reference light the divided beam to the light intensity measuring unit 28 through an output terminal OUT$_{V+6}$. Accordingly, light having discrete wavelengths of 1200 nm, 1300 nm, and 1600 nm may be radiated onto the tissue surface of the target material 22.

Consequently, an apparatus and method for measuring a concentration of a component according to an embodiment of the present invention radiates light having discrete wavelengths of, for example, 1200 nm, 1300 nm, and 1600 nm, generated as described above, at a target material 22, measures the intensity of light reflected from or transmitted through the target material 22 using the light intensity measuring unit 28, analyzes differences in the quantity of light of different wavelengths using the concentration measuring unit 30 based on the measured intensity of light, thereby measuring the concentration of a component of blood.

The wavelengths of 1064 nm, 1200 nm, 1300 nm, 1480 nm, and 1600 nm mentioned in the description of the operation of the apparatus shown in FIG. 10 have been introduced as examples to illustrate an embodiment of the present invention. The configuration and operation of the apparatus of FIG. 10 are not limited to these examples. In other words, the apparatus of FIG. 10 may receive light having a wavelength different from the above-described wavelengths through the input terminal IN4, and generate light having at least one discrete wavelength different from the above-described wavelengths through the output terminals OUT$_{V+4}$ through OUT$_{V+6}$.

According to an embodiment of the present invention, the first wavelength conversion unit 12 shown in FIG. 1 may be replaced with the wavelength converter shown in FIG. 7 in order to generate light having a wavelength of 2100 nm. Here, if an Ho:YAG or Tm:YAG laser at 2 $\mu$m is used as the pumping light source 10, and if the optical fiber 192 is made of silica or doped with germanium, light having wavelengths ranging from 2.1 $\mu$m to 2.2 $\mu$m may be radiated at the target material 22.

When the first wavelength conversion unit 12 is replaced with a wavelength converter shown in FIG. 7 in the apparatus of FIG. 1, if light having a wavelength of 1470 nm is generated using an OPO laser as the pumping light source 10, and if the core 194 of the optical fiber 192 is made of silica or doped with germanium, light having wavelengths of 1470 nm, 1572 nm, and 1689 nm may be radiated at the target material 22. In this case, if the pumping light source 10 generates light having a wavelength of 1520 nm, light having a wavelength of 1628 nm may be radiated at the target material 22.

An apparatus and method for measuring a concentration of a component according to an embodiment of the present invention may improve an SNR compared with a conventional apparatus and method for measuring the concentration of a component. For example, under the condition that a wavelength of 1689 nm in which the band width of a spectrum is 10 nm is used as a wavelength being absorbed into a particular component, when a 100 W CW lamp light source is used according to a conventional method, the value of a peak power at a wavelength of 1689 nm does not exceed 5–10 mW. However, when a laser having a Full Width at Half Maximum (FWHM) of 10 ns and a repetition rate of 10 Hz is used as the pumping light source 10 according to an embodiment of the present invention, energy of several tens of $\mu$J may be generated at a wavelength of 1689 nm, and the value of a peak power is several kW. Accordingly, the present invention greatly increases the quantity of light radiated at a target material, thereby improving the SNR, as compared with the conventional method.

As described above, an apparatus and method for measuring a concentration of a component of a target material according to an embodiment of the present invention may easily generate light having discrete wavelengths corresponding to absorption spectra of components in the target material by doping the cores of optical fibers with various materials in different ways or combining wavelength conversion units. According to an embodiment of the present invention, since light having a large peak power is radiated at the target material 22, greater intensities of light may be measured, so the SNR can be improved as compared to the prior art. Since the light radiated at the target material 22 has only discrete wavelengths not a continuous spectrum, the present invention does not need a band-pass filter used in the prior art for selecting a particular wavelength. The present invention may invasively or non-invasively measure the concentration of a component. In addition, since the present invention is able to remarkably decrease average energy consumed at the target material 22, for example, at a tissue interface of an organism, to several hundreds of $\mu$W compared to average energy of mW-W when a conventional CW light source is used, the present invention prevents the characteristics of organic tissue from changing due to heat, thereby measuring the concentration of a component without damaging the organic tissue. Moreover, compared to a conventional method using the combination of a plurality of laser diodes (LDs) or light emitting diodes (LEDs) to increase power at a particular wavelength, the present invention may easily achieve alignment and realize miniaturization and lightweight due to technological developments of a laser used as the pumping light source 10 and of optical fibers.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An apparatus for measuring a concentration of a component of a target material, the apparatus comprising:

a pumping light source for emitting light having a single wavelength having peak power of at least a predetermined value;

a first wavelength conversion unit for converting light incident from the pumping light source into light having at least one discrete wavelength and outputting the converted light;

a first beam splitting unit for splitting the converted light incident from the first wavelength conversion unit into light beams and directing a first light beam at the target material;

a reference light generator for converting a second light beam generated by the splitting performed in the first beam splitting unit to be parallel, dividing the parallel light beam by wavelengths, and outputting the result of the division as reference light;

a first collimating unit for converting light transmitted through the target material to be parallel and outputting the parallel light;

a light intensity measuring unit for measuring the intensity of light incident from the first collimating unit and the intensity of the reference light, by wavelengths, using the reference light; and a concentration measuring unit for measuring the concentration of the component based on the intensities measured by the light intensity measuring unit by wavelengths.

2. The apparatus as claimed in claim 1, wherein the concentration measuring unit comprises:

an amplifier for amplifying the intensity measured by the light intensity measuring unit by wavelengths and outputting the result of the amplification;

an analog-to-digital converter (ADC) for converting the result of the amplification into a digital signal and outputting the digital signal; and a signal processor for analyzing the digital signal to measure the concentration of the component of the target material.

3. The apparatus as claimed in claim 1, further comprising a first condensing lens for condensing the first light beam generated by the splitting performed in the first beam splitting unit and transmitting the result of the condensing at the target material.

4. The apparatus as claimed in claim 1, further comprising an index-matching unit for transmitting the first one of the light beams generated by the splitting performed in the first beam splitting unit at the target material.

5. The apparatus as claimed in claim 1, further comprising a wavelength divider for dividing light incident from the first collimating unit by wavelengths and outputting the result of the division to the light intensity measuring unit, wherein the light intensity measuring unit measures the intensity of light incident from the wavelength divider and the intensity of the reference light, by wavelengths.

6. The apparatus as claimed in claim 1, wherein the first wavelength conversion unit comprises a first through Y-th wavelength converters, wherein Y is 1 or a positive integer greater than 1, connected in series, and the y-th, wherein $1 \leq y \leq Y$, wavelength converter condenses incident light and converts the incident light into light having at least one wavelength and converts the light having at least one wavelength to be output in parallel.

7. The apparatus as claimed in claim 6, wherein the y-th wavelength converter comprises:

a light condensing unit for condensing incident light and outputting the condensed light;

an optical fiber for receiving the condensed light from the light condensing unit and outputting the light having at least one wavelength; and a second collimating unit for converting the light received from the optical fiber to be parallel and outputting the converted light.

8. The apparatus as claimed in claim 7, wherein the light condensing unit comprises a second condensing lens for condensing the incident light and outputting the condensed light to an incident surface of a core of the optical fiber.

9. The apparatus as claimed in claim 7, wherein the light condensing unit comprises tapered fiber for condensing the incident light and outputting the condensed light to an incident surface of a core of the optical fiber.

10. The apparatus as claimed in claim 9, wherein the tapered fiber is fusion-spliced to the optical fiber.

11. The apparatus as claimed in claim 7, wherein a core of the optical fiber is made of pure silica.

12. The apparatus as claimed in claim 7, wherein a core of the optical fiber is doped with $GeO_2$.

13. The apparatus as claimed in claim 7, wherein a core of the optical fiber is doped with $P_2O_5$.

14. The apparatus as claimed in claim 7, wherein the optical fiber is a single mode optical fiber.

15. The apparatus as claimed in claim 7, wherein the optical fiber is a multi-mode optical fiber.

16. The apparatus as claimed in claim 7, wherein the optical fiber is a step-index optical fiber.

17. The apparatus as claimed in claim 7, wherein the optical fiber is a graded-index optical fiber.

18. The apparatus as claimed in claim 1, wherein the target material is selected from a group consisting of a living body, an organism and a sample cuvette.

19. The apparatus as claimed in claim 1, wherein the pumping light source is selected from a group consisting of a pulse laser and a continuous wave (CW) laser.

20. The apparatus as claimed in claim 19, wherein the pulse laser is one selected from the group consisting of a Nd:YAG laser, a Ho:YAG laser, a Tm:YAG laser, an optical parametric oscillation (OPO) laser, a solid-state laser, and an optical fiber laser.

21. The apparatus as claimed in claim 1, wherein the light intensity measuring unit comprises a near infrared light intensity measuring unit for measuring the intensity of light incident from the first collimating unit and the intensity of the reference light, by wavelengths.

22. The apparatus as claimed in claim 1, wherein the light intensity measuring unit comprises an array light intensity measuring unit for measuring the intensity of light incident from the first collimating unit and the intensity of the reference light, by wavelengths.

23. An apparatus for measuring a concentration of a component of a target material, the apparatus comprising:

a pumping light source for emitting light having a single wavelength having peak power of at least a predetermined value;

a second through 2V-th beam splitting units, wherein V is at least 2;

a second through (V+1)-th wavelength conversion units;

a total reflector;

a reference light generator for converting a light beam generated by splitting performed in each of the (V+1)-th through the 2V-th beam splitting units to be parallel, dividing the parallel light by wavelengths, and outputting the result of the division as reference light;

a first collimating unit for converting light transmitted through the target material to be parallel and outputting the parallel light;

a light intensity measuring unit for measuring the intensity of light incident from the first collimating unit and the intensity of the reference light, by wavelengths, using the reference light; and a concentration measuring unit for measuring the concentration of the component based on the intensities measured by the light intensity measuring unit by wavelengths, wherein the second beam splitting unit splits light incident from the pumping light source into light beams and outputs one of the light beams to the second wavelength conversion unit, the v-th ($3 \leq v \leq V$) beam splitting unit receives and splits one of light beams generated by the splitting performed in the (v−1)-th beam splitting unit into light beams and outputs one of the light beams to a v-th wavelength conversion unit, the total reflector totally reflects one of the light beams generated by the splitting performed in the V-th beam splitting unit to the (V+1)-th wavelength conversion unit, the w-th ($2 \leq w \leq V+1$) wavelength conversion unit converts incident light into light having at least one discrete wavelength and outputs the converted light, and the (V+w−1)-th beam splitting unit splits light incident from the w-th wavelength conversion unit into light beams and outputs one of the light beams at the target material.

24. The apparatus as claimed in claim 23, wherein the concentration measuring unit comprises:
- an amplifier for amplifying the intensity measured by the light intensity measuring unit by wavelengths and outputting the result of the amplification;
- an analog-to-digital converter (ADC) for converting the result of the amplification into a digital signal and outputting the digital signal; and a signal processor for analyzing the digital signal to measure the concentration of the component of the target material.

25. The apparatus as claimed in claim 23, further comprising a first condensing lens for condensing one of the light beams generated by the splitting performed in the x-th beam splitting unit, wherein x is between V+1 and 2V inclusive, and transmitting the result of the condensing at the target material.

26. The apparatus as claimed in claim 23, further comprising an index-matching unit for transmitting one of the light beams generated by splitting performed in the x-th beam splitting unit, wherein x is between V+1 and 2V inclusive, at the target material.

27. The apparatus as claimed in claim 23, further comprising a wavelength divider for dividing light incident from the first collimating unit by wavelengths and outputting the result of the division to the light intensity measuring unit, wherein the light intensity measuring unit measures the intensity of light incident from the wavelength divider and the intensity of the reference light, by wavelengths.

28. The apparatus as claimed in claim 23, wherein each of the second through (V+1)-th wavelength conversion units comprises a first through Y-th wavelength converters, wherein Y is 1 or a positive integer greater than 1, connected in series, and the y-th, wherein $1 \leq y \leq Y$, wavelength converter condenses incident light and converts the incident light into light having at least one wavelength and converts the light having at least one wavelength to be output in parallel.

29. The apparatus as claimed in claim 28, wherein the y-th wavelength converter comprises:
- a light condensing unit for condensing incident light and outputting the condensed light;
- an optical fiber for receiving the condensed light from the light condensing unit and outputting the light having at least one wavelength; and
- a second collimating unit for converting the light received from the optical fiber to be parallel and outputting the converted light.

30. The apparatus as claimed in claim 29, wherein the light condensing unit comprises a second condensing lens for condensing the incident light and outputting the condensed light to an incident surface of a core of the optical fiber.

31. The apparatus as claimed in claim 29, wherein the light condensing unit comprises tapered fiber for condensing the incident light and outputting the condensed light to an incident surface of a core of the optical fiber.

32. The apparatus as claimed in claim 31, wherein the tapered fiber is fusion-spliced to the optical fiber.

33. The apparatus as claimed in claim 29, wherein a core of the optical fiber is made of pure silica.

34. The apparatus as claimed in claim 29, wherein a core of the optical fiber is doped with $GeO_2$.

35. The apparatus as claimed in claim 29, wherein a core of the optical fiber is doped with $P_2O_5$.

36. The apparatus as claimed in claim 29, wherein the optical fiber is a single mode optical fiber.

37. The apparatus as claimed in claim 29, wherein the optical fiber is a multi-mode optical fiber.

38. The apparatus as claimed in claim 29, wherein the optical fiber is a step-index optical fiber.

39. The apparatus as claimed in claim 29, wherein the optical fiber is a graded-index optical fiber.

40. The apparatus as claimed in claim 23, wherein the target material is selected from a group consisting of a living body, an organism and a sample cuvette.

41. The apparatus as claimed in claim 23, wherein the pumping light source is selected from a group consisting of a pulse laser and a continuous wave (CW) laser.

42. The apparatus as claimed in claim 41, wherein the pulse laser is one selected from the group consisting of a Nd:YAG laser, a Ho:YAG laser, a Tm:YAG laser, an optical parametric oscillation (OPO) laser, a solid-state laser, and an optical fiber laser.

43. The apparatus as claimed in claim 23, wherein the light intensity measuring unit comprises a near infrared light intensity measuring unit for measuring the intensity of light incident from the first collimating unit and the intensity of the reference light, by wavelengths.

44. The apparatus as claimed in claim 23, wherein the light intensity measuring unit comprises an array light intensity measuring unit for measuring the intensity of light incident from the first collimating unit and the intensity of the reference light, by wavelengths.

45. A method for measuring a concentration of a component of a target material, the method comprising:
- (a) emitting light having a single wavelength having peak power of at least a predetermined value;
- (b) converting the emitted light into light having at least one discrete wavelength;
- (c) splitting the converted light into light beams, directing a first light beam at the target material, converting a second light beam to be parallel, and dividing the parallel converted second light beam by wavelengths to generate reference light;
- (d) converting light transmitted through the target material to be parallel;
- (e) measuring the intensity of the parallel converted light obtained in (d) and the intensity of the reference light, by wavelengths; and
- (f) measuring the concentration of the component based on the intensities measured by wavelengths.

46. The method as claimed in claim 45, further comprising:
- (g) splitting the light emitted in (a) into at least two light beams,
- wherein (b) comprises converting each of the at least two light beams obtained in (g) into light having at least one wavelength, and (c) comprises splitting the converted light obtained in (b) into light beams, radiating a first one of the light beams at the target material, converting a second one of the light beams to be parallel, and dividing the parallel converted second light beam by wavelengths to generate the reference light.

47. The method as claimed in claim 45, wherein (f) comprises:
- amplifying the intensities measured by wavelengths in (e);
- converting the result of amplification into a digital form to generate a digital signal; and
- analyzing the digital signal to measure the concentration of the component of the target material.

48. The method as claimed in claim 45, further comprising condensing the first one of the light beams obtained in (c) and transmitting the result of condensing at the target material.

* * * * *